United States Patent
Eliaz

(10) Patent No.: US 8,916,541 B2
(45) Date of Patent: Dec. 23, 2014

(54) SYNERGISTIC COMBINATION OF HONOKIOL AND MODIFIED CITRUS PECTIN IN CANCER THERAPY

(75) Inventor: Issac Eliaz, Sebastopol, CA (US)

(73) Assignee: Better Health Publishing, Inc., Santa Rosa, CA (US)

(*) Notice: Subject to any disclaimer, the term of this patent is extended or adjusted under 35 U.S.C. 154(b) by 427 days.

(21) Appl. No.: 12/984,843

(22) Filed: Jan. 5, 2011

(65) Prior Publication Data

US 2012/0171228 A1 Jul. 5, 2012

(51) Int. Cl.
| | |
|---|---|
| A61K 31/732 | (2006.01) |
| A61K 39/00 | (2006.01) |
| A61P 35/00 | (2006.01) |
| A61K 39/39 | (2006.01) |
| A61K 31/05 | (2006.01) |
| A61K 45/06 | (2006.01) |

(52) U.S. Cl.
CPC ............ *A61K 39/39* (2013.01); *A61K 31/05* (2013.01); *A61K 31/732* (2013.01); *A61K 45/06* (2013.01); *A61K 2039/55583* (2013.01)
USPC ............. 514/54; 514/19.3; 424/184.1; 536/2

(58) Field of Classification Search
CPC . A61K 2300/00; A61K 31/05; A61K 31/732; A61K 2039/55583; A61K 39/39; A61K 45/06; G01N 33/574; G01N 33/57411; G01N 33/57415; G01N 33/57419
USPC ...................... 514/54, 19.3; 424/184.1; 536/2
See application file for complete search history.

(56) References Cited

U.S. PATENT DOCUMENTS

| | | | |
|---|---|---|---|
| 6,274,566 B1 | 8/2001 | Eliaz et al. | |
| 6,462,029 B1 | 10/2002 | Eliaz | |
| 7,026,302 B2 | 4/2006 | Eliaz | |
| 7,451,871 B2 | 11/2008 | Schuurs | |
| 2004/0223971 A1* | 11/2004 | Chang et al. | 424/155.1 |
| 2008/0300298 A1* | 12/2008 | Arbiser et al. | 514/450 |

OTHER PUBLICATIONS

Liu, et al., "Anti-Tumor Effect of Honokiol Alone and in Combination with Other Anti-Cancer Agents in Breast Cancer", European Journal of Pharmacology 591 (2008) 48-51.
Nangia-Makker, et al., "Inhibition of Human Cancer Cell Growth and Metastasis in Nude Mice . . . ", Journal of the National Cancer Institute, vol. 94, No. 24, Dec. 18, 2002.
Shigemura, et al., "Honokiol, a Natural Plant Product, Inhibits the Bone Metastatic Growth of Human Prostate Cancer Cells", Cancer, Apr. 1, 2007, vol. 109, No. 7.

(Continued)

*Primary Examiner* — Savitha Rao
(74) *Attorney, Agent, or Firm* — Steven B. Kelber

(57) ABSTRACT

The invention comprises the administration of an amount of honokiol (HNK) and Modified Citrus Pectin (MCP) or similar pectin or alginate in amounts synergistic to inhibit cancer. The inhibition can be of the formation of cancer, the progression of a cancer already formed, or the transformation of a primary cancer to a metastatic one. HNK and MCP appear to be synergistic across their effective ranges, and the synergy may be due in part to the binding of galectin-3 on the surface of tumor cells by MCP, which better presents the cell for the cytotoxic effects of HNK. Compositions of matter which combine the two agents, HNK and MCP, in synergistic amounts intended for daily administration are also contemplated. The administration of MCP and HNK may be combined with the administration of conventional anti-cancer therapeutics.

16 Claims, 9 Drawing Sheets

(56) References Cited

OTHER PUBLICATIONS

Yan, et al., "PectaSol-C Modified Citrus Pectin Induces Apoptosis and Inhibition of Proliferation in Human and Mouse . . . ", Integrative CAncer Therapies 9(2), pp. 197-203. (2010).

Yang, et al., "Down-Modulation of Bcl-XL, Release of Cytochrome c and Sequential Activation of Caspases . . . " Biochem. Pharmacol. May 1, 2002;63(9):1641-51.

Ahn, et al., "Honokiol Potentiates Apoptosis, Suppresses Osteoclastogenesis, and Inhibits Invasion . . . ", Mol. Cancer Res. 2006; 4(9), Sep. 2006.

Azemar, et al., "Clinical Benefit in Patients with Advanced Solid Tumors Treated with Modified . . . ", Clinical Medicine Oncology 2007:1 73-80.

Chen, et al., "Honokiol: A Potent Chemotherapy Candidate for Human Colorectal Carcinoma", World J. Gastroenterol Dec. 2004; 10(23): 3459-3463.

Dharma Biomedical, "Final Report—T-helper/inducer Cell, T-Cytotoxic/suppressor Cell, B-Cell and NK-Cell . . . ", pp. 1-12, Dec. 10, 2010.

Garcia, et al., "Honokiol Suppresses Survival Signals Mediated by Ras-Dependent Phospholipase . . . ", Clin. Cancer REs. 2008;14(13) Jul. 1, 2008.

Glinsky, et al., "Modified Citrus Pectin Anti-Metastatic Properties: One Bullet, Multiple Targets", Carbohydr. Res. (2008).

Guess, et al., "Modified Citrus Pectin (MCP) INcreases the Prostate-Specific Antigen . . . ", PRostate Cancer and Prostatic Diseases (2003) 6, 301-304.

Gunning, et al., "Recognition of Galactan Components of Pectin by Galectin-3", FASEB Journal, vol. 23, Feb. 2009 pp. 415-424.

Hahm, et al., "Honokiol, a Constituent of Oriental Medicinal Herb *Magnolia officinalis*, Inhibits Growth . . . " Clin. Cancer REs. 2008;14(4) Feb. 15, 2008.

Kay, et al., "Effect of Citrus Pectin on Blood Lipids and Fecal Steroid Excretion in Man", Am. Journal of Clinical Nutrition 30: Feb. 1977, pp. 171-175.

\* cited by examiner

SYNERGISTIC COMBINATION OF HONOKIOL AND MODIFIED CITRUS PECTIN IN CANCER THERAPY

BACKGROUND OF THE INVENTION

1. Field of the Invention

The present invention relates to regimens and therapeutics intended to inhibit the formation, progression and metastatic conversion of a variety of cancers in mammals, including humans. Cancers effectively targeted by this regimen include solid tumors of a wide variety, and include primary tumors, as well as secondary cancers, such as a prostate, cancer metastasizing into bone cancer. Specific cancer targets include liver cancer, prostate cancer, breast cancer, colorectal cancer, stomach cancer, esophageal cancer, lung cancer, nasopharyngeal cancer, thyroid cancer, ovarian cancer, uterine cancer, multiple myeloma, leukemia, lymphoma, melanoma, sarcoma, ovarian, uterine, nasopharyngeal, brain, thyroid or kidney cancer. Although the inventors have not yet had the opportunity to test this regimen against all cancer types, it does not appear restricted in its applicability to any given cancer type or line, as galectin-3 molecules are present in a great variety of tumors and the molecular synergistic effects are not tumor specific. The invention is also effective against non-solid tumors such as leukemias and lymphomas.

The regimen provided depends on an observed synergy between two documented anticancer agents, honokiol (derived from the magnolia plant originally) and modified citrus pectin, citrus pectin that is broken down either through heat, hydrolysis or enzymatic degradation to lower molecular weight and partially esterified galacturonic acid moieties. Instead of MCP which is widely available from the Assignor of this application, EcoNugenics Inc. of Santa Rosa Calif. as both Pecta-Sol® and PectaSol-C® Modified Citrus Pectin or MCP, similarly modified alginates may be employed.

2. Background of the Invention

MCP and Honokiol are both well-known non-toxic and well-tolerated agents effective in a variety of treatments. Honokiol has been used for many years in Chinese herbal therapy annals, and been shown to be effective in inhibiting platelet aggregation, protection of the myocardium against ischemic damage and exhibits anti-inflammatory, antibacterial and anti-oxidative properties. Hahm et al, *Clin. Cancer Res.* 14(4) (2008). Honokiol has also been demonstrated to be an effective anti-cancer agent. It has been shown to induce apoptosis in lung cancer cells, Yeng et al, *Biochem. Pharmacol.* 63:1641-51 (2002) probably through caspase activation, and been shown to be effective in vivo against colorectal cancer and breast cancer in nude mice bearing transplanted tumors. Wang et al, *World J. Gastoenterol.* 10:3459-63 (2004).

Independent of mechanistic explanations, Honokiol has been shown to inhibit the formation of cancer cells, inhibit the progression of cancer cells and target cancer cells for destruction through apoptosis and inhibit spontaneous metastases of established cancer cells. This has been demonstrated in vitro against cancer cell lines, and in vivo in mammals including rodents and humans. Importantly, promising effects against cell lines have been repeatedly demonstrated to be echoed in in vivo testing. Shigemura et al, *Cancer:* 109(7) 1279-89 (2007) and Bai, et al, *J. Biol. Chem.:* 278, 35501-7, (2003) and Ahn et al, *Mol. Cancer. Res.:* 4(9) 621-32 (2006). Honokiol is widely available, and can be obtained from Herbal Extracts Plus of Croyden, Pa. and Century Supplements of Vancouver, British Columbia, as well as a large number of herbal supplement providers. It is non-toxic and well tolerated, and has effectiveness, in various indications, at values of 2-500 mg/kg/day, with optimum values for anti-cancer applications in the range of 25-150 mg/kg/day.

Modified Citrus Pectin (MCP) and its corresponding alginate derivatives, polysaccharides having a molecular weight of less than 40,000 daltons, are well established as therapeutic agents. U.S. Pat. No. 7,026,302 as well as related U.S. Pat. Nos. 6,462,029 and 6,274,566 describe MCP products and alginates prepared by either hydrolysis or enzymatic digestion shown to be effective in treatment of a wide variety of poisoning and disease states. The disclosure of these patents is incorporated herein-by-reference. U.S. Pat. No. 7,451,871 also discloses the use of these modified citrus pectins and related compounds having a low enough molecular weight to be easily absorbed and having partially esterified galacturonic acid moieties as aids in controlling cancer metastases by binding the cancer emboli in the blood stream. Both the '871 patent, and U.S. patent application Ser. No. 11/485,955, which discloses that MCP can be used to enhance the immune system response of mammals, are incorporated herein-by-reference.

The antineoplastic effect of MCP is well documented. Gunning et al, *FASEB J.*, Vo. 23, 415-424 (2009) first reviews the demonstrated effectiveness of MCP against a variety of cancers, both in terms of inhibiting progression and metastases, and establishes that these modified pectins and alginates bind in vivo, the mammalian protein galectin-3. Galectin-3 (Gal3) is a protein implicated in a number of different cancer cell progressions and metastatic conversions, and by binding this protein, the transformation of cells into cancerous cells may be inhibited, and the progression of existing cancers slowed. In addition to binding cancer emboli and suppressing metastases through these processes, MCP may also be effective in suppressing the conversion to metastatic forms. Yan and Katz, Int. Cancer Ther. 9 (2), 197-203 (2010). MCP has been shown to be effective in the treatment of, and inhibition of, prostate cancer, Pienta et al, *J. Natl. Cancer Inst.*, 24, 1854-62 (2002) as well as lung cancer, fibrosarcoma and melanoma. Kay et al, *Am. J. Clin. Nutr.*, 30, 171-175 (1997) as well as other solid tumors, such as breast cancer, liver cancer and colorectal cancer. MCP appears to bind to Gal3 present on the surface of tumor cells, both solid and non-solid, which inhibits those tumors from developing or transforming. Azemar et al, *Oncology*, 1, 73-80 (2007). The immunomodulating effect of MCP may be due to a similar phenomenon, where binding triggers certain chemical releases or inhibits inflammation, cell adhesion and cell migration. Id.

Accordingly, those of skill in the art are aware of two well tolerated, non-toxic agents, honokiol and MCP, both substances commercially available in high levels of purity, that are effective as anti-cancer agents. They are administrable over a wide variety of protocols, including IM and IV and parentaral administration, as well as subcutaneous administration and by adsorption through mucosal membranes, desirably through rectal and vaginal suppositories. Perhaps most importantly, they have been shown to be effective as orally administered, and may be taken daily, in one dose or in multiple doses per day, as part of a dietary regimen. They have been demonstrated to be safe and effective over a wide range of dosages, with honokiol being shown as effective over 10-500 mg/kg/day, and MCP at levels of 15-700 mg/kg/day (1-50 g/day), with an optimum level, for exhibiting effectiveness against cancer, at about 75-300 mg/kg/day (5-20 g/day.)

Neither of these agents is completely effective on its own against particularly intractable cancers, such as liver and colorectal cancer cells. Honokiol has been administered with low-dose docetaxel (to avoid systemic effects). The combination gave, to a limited degree, an additive effect improving the effectiveness over the administration of honokiol alone, but not a substantial improvement over conventional chemotherapeutic administration. Shigemura et al, p. 1280. As noted in the art, even securing additive effects for the administration of two agents directed against the same cancer or cancers is rare. Typically, only the impact of the more effective of two drugs is observed, with little improvement secured where both drugs are administered at therapeutic effective levels. What is frequently desired, but rarely observed, is a synergistic combination of two agents administered against a common target or disease condition. By definition, such synergy is unpredictable. Those of skill in the art continue to search for such a combination to combat the transformation of cells into cancerous cells, the progression of these cancers, and the transformation of those cancers to metastatic cancers.

SUMMARY OF THE INVENTION

It is Applicant's discovery that a combination of honokiol and MCP or similar low molecular weight pectin, or another source of galacturonic acid moieties that bind Gal3 such as low molecular weight alginates or other similar water soluble polyuronide is effective in inhibiting the progression of cancers, including drug resistant or intractable cancers like metastatic prostate cancer, liver cancer, breast cancer and colorectal cancer among others. Although both honokiol and MCP have been shown, separately, to be effective antineoplastic agents, when combined, the result is more than additive, it is synergistic. The inhibiting effect of the combined regimen of honokiol and MCP appears to provide profound effectiveness in inhibiting the development, progression and transformation of cancers of a wide variety.

BRIEF DESCRIPTION OF THE DRAWINGS

The accompanying drawings, which are incorporated herein and constitute part of this Specification, illustrate exemplary embodiments of the invention, and, together with the general description given above and the detailed description given below, serve to explain the features of the invention.

FIG. 3 reflects an increase in T-cytotoxic/suppressor lymphocyte activation upon administration of MCP.

FIG. 4 shows the percentage increase T-helper/inducer lymphocyte activation upon administration of MCP.

FIG. 5 gives the percentage increase T-cytotoxic/suppressor lymphocyte activation upon administration of MCP.

FIG. 6 reflects the increase in B-cell activation achieved by MCP administration.

FIG. 7 shows the percentage increase of B-cell activation due to MCP administration as compared with positive controls (T2CA and PWM).

FIG. 8 reflects the increase in NK-cell activation achieved by MCP administration.

FIG. 9 shows the percentage increase of NK-cell activation due to MCP administration as compared with positive controls (T2CA and PWM).

DETAILED DESCRIPTION OF THE INVENTION

Figure 1A:
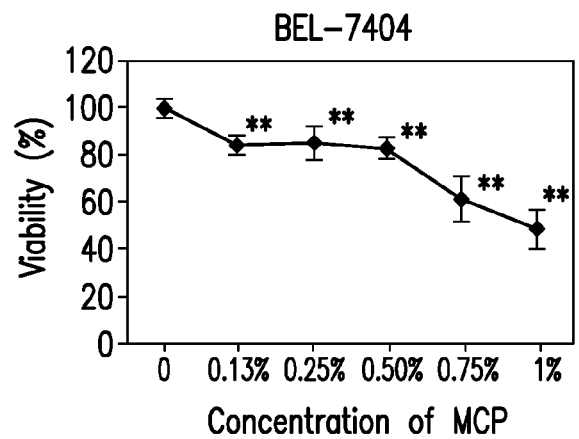
FIGS. 1A, B and C reflect the effects on the administration of MCP or honokiol (HNK) or its combination, respectively, on liver cells FIG. 2 reflects an increase in T-helper/inducer lymphocyte activation upon administration of MCP.

Applicant's invention begins with the recognition that MCP has an important stimulatory effect on the immune system. The immunomodulatory effects of MCP may be involved in the synergy observed between these two agents. The synergy may also be dependent on the anti-inflammatory properties of HNK, and the activation of additional pathways when co-administered. As one possible explanation, although Applicants do not wish to be bound by this theory, it is believed that the immunomodulatory effect of MCP allows a better presentation of the cancer cell, or potential cancer cell, to permit the HNK to better effect apoptosis and cell killing. Thus, although both MCP and HNK are noted for their ability to inhibit the formation, progression and transformation of cancer cells in vitro and in vivo, their action appears to be through distinct modes. The ability of MCP to bind the Gal-3 present on the surface of the cancer cell, and enhance an immune reaction in vivo, is believed to in turn permit HNK to kill cancer cells, or inhibit their growth, much more effectively. Thus, their combined effect is synergistic, providing cancer inhibition in excess of the results obtained by the administration of either agent, alone.

By synergistic amount, in this application, reference is made to the effect obtained by administering effective amounts of both MCP and HNK simultaneously. A synergistic result is one where the inhibition of cancer is greater than the same results that are obtained by administering the identical amount of MCP alone, plus the inhibition achieved by administering the same amount of HNK alone. The two appear synergistic over their conventional ranges, but where the term appears in this application for patent, it is intended to mean an amount of MCP or HNK sufficient to achieve the synergy in result of administration of the remaining agent observed herein. In general, a synergistic result is obtained where HNK is administered in amounts of approximately 10-500 mg/kg/day with a preferred range being 15 mg/kg/day up to 300 mg/kg/day and MCP is administered in the range of 15-700 mg/kg/day (1-50 g/day). The values given above are for oral administration. Those of skill in the art are well acquainted with methods to titrate from those dosages to appropriate and equivalent dosages for IV, IM, IP subcutaneous or mucosal penetration modes of administration.

The goal of administration of MCP and HNK is inhibition of cancer. Inhibition refers to preventing and slowing the formation, growth and transformation of the cancers addressed by the regimen of this invention. In one form, the regimen is a daily intake of MCP and HNK in the synergistic range. This inhibits the formation of cancer, and the progression of cancers that may be localized or early stage, particularly precancerous cells and conditions. Thus, daily consumption of a synergistic amount of HNK and MCP forms one important aspect of this invention. Inhibition of cancer, as used herein, also refers to inhibiting or slowing the growth of established cancers. This is particularly meaningful in slowing the growth of solid tumors. Thus, the ability of MCP to bind Gal3 or otherwise present cancer cells for the anti-cancer cytotoxic effects of HNK forms a second aspect of this invention. Again, administration of a synergistic combination of HNK and MCP is called for. In this second embodiment, dosage levels may be higher than the prophylactic model, A value of 8-50 gram/day (100-700 mg/kg/day) MCP and 25-500 mg/kg/day HNK may be appropriate to inhibit the growth of developed cancers, even advanced cancers. As for the prevention of the formation of cancers, in this mode of therapeutic treatment, optimum effect is observed through daily administration of MCP and HNK in synergistic amounts. In this regard, the administration of HNK and MCP in synergistic amounts may be combined with administration of established anti-cancer therapies such as doclitaxel or paclitaxel, or doxorubicin, at regular or reduced levels, drugs which have demonstrated effectiveness against certain cancers, but are widely recognized as systemically toxic at levels that may be required for effectiveness. HNK and MCP can also be combined with other therapeutic agents such as botanicals, minerals and vitamins, example being Quercetin, curcumin, ECGC form green tea extract, artemisinin, sodium phenyl butyrate, Resveratrol (3,5,4'-trihydroxy-trans-stilbene), Vitamin D-3, and others. Similarly, established immunotherapy and biologics, such as antibodies targeting vascular endothelial growth factor (VEGF) endothelial growth factor (EGFR) and other targeted antibodies, like trastuzumab (Herceptin®) and bevacizumab (Avastin®) demonstrated effective against cancer can be administered together with the synergistic combination of HNK and MCP to reduce necessary dosages for these immunotherapies and biologics, or improve effectiveness at established dosages. The administration of HNK and MCP in synergistic amounts provides a basis for administering toxic agents at a lower, sub-toxic amount to achieve enhanced cancer treatment. Contrariwise, the administration of a chemotherapeutic agent at its normal effective dosage, combined with a synergistic amount of MCP and HNK, may be used to actually boost the effectiveness of the chemotherapeutic agent administered alone.

As those of skill in the art are well aware, for many cancers, mortality is linked to the transformation of the primary cancer into a metastatic cancer, giving rise to a variety of secondary metastases, including highly intractable cancers like bone and liver cancer. In a third embodiment of this invention, cancer inhibition is measured in the inhibition and slowing of a primary cancer's transformation to metastatic cancer and inhibiting the spread and formation of metastases. In many cases, long-term inhibition of the transformation of primary cancers may provide sufficient time for traditional chemotherapeutic and radioactive therapies to effectively reduce or eliminate the primary cancer-therapies which would fail in the face of transformation. It can also provide for longer remissions, and for more effective treatment in general in preventing the metastatic process. The co-administration of MCP and HNK in synergistic amounts may be used to slow or delay both the transformation of a primary cancer into a metastatic one, and control or inhibit the spread or dissemination of metastases.

MCP Exhibits Immune System Stimulation

Studies were undertaken by an independent laboratory to look at immune system cell activation as a consequence of the administration of MCP from EcoNugenics, Inc.

In vitro lymphocyte activation represents a standard approach for evaluating cell-mediated responses to a variety of stimuli including immunostimulatory botanical extracts. The FastImmune assay system monitors the expression of the early activation marker CD69 in whole blood after stimulation with extracts. CD69 is expressed in all activated lymphocytes (T-lymphocytes, B-lymphocytes and NK-cells) and hence it represents a generic marker to monitor individual subset responses to specific stimuli.

T-lymphocyte subsets can be identified and quantified by using fluorochrome-labeled antibody combinations such as CD4/CD69/CD3 and CD8/CD69/CD3. CD4 antigen is expressed on the T-helper/inducer lymphocyte subset (CD3/CD4). CD8 antigen is expressed on the human suppressor/cytotoxic T-lymphocyte subset (CD3/CD8). Once activated both CD4 and CD8 positive T cells express CD69.

CD19 antigen is present on human B lymphocytes at all stages of maturation and is not present on resting or activated T-lymphocytes. CD19/CD69/CD45 combination can be used to identify activated B cell population. CD56 antigen is present on natural killer (NK) cells and antigen intensity increases with NK-cell activation. Hence, CD56/CD69/CD45 combination can be used to identify activated NK-cells.

PMCP was initially solubilized in phosphate buffered saline (PBS) and dimethyl sulfoxide (DMSO) for the assay. Solubility in PBS was determined to be greater than DMSO. The solubility of PMCP (Lot #30324) in PBS was ~76.4%. The volume was adjusted to get accurate amounts of each compound for treatment based on solubility factor.

Blood samples were collected from healthy volunteers and 250 µl blood sample were incubated in 48-well plates with increasing concentrations of compound along with appropriate positive controls (recommended by Becton Dickinson Biosciences, CA) for each subset. CD2/CD2R and Phorbol ester (PMA) were used as controls for T-lymphocyte activation studies. Pokeweed (PWM) mitogen was used as positive control for B-cell activation and IL-2 was used for activating NK-cells in blood cultures. T2CA, a characterized polysaccharide complex evaluated in these assays was also used as a control. The blood cultures were incubated at 37° C. in a $CO_2$ incubator for 24 h. On the next day, 20 µl of specific antibody mix, [CD4-FITC/CD69-PE/CD45-PerCP (T-helper/inducer cell activation), CD8-FITC/CD69-PE/CD3-PerCP (T-cytotoxic/suppressor cell activation), CD19-FITC/CD69-PE/CD45-PerCP (B-cell activation) and CD56-FITC/CD69-PE/CD45-PerCP (NK-cell activation)] was dispensed into separate flow tubes and 50 µl blood sample was mixed with antibody and incubated for 30 minutes at room temperature in the dark. The blood-antibody mix was lyzed in a Coulter Epics Q-prep work station using Immunoprep kit and run on a Beckman Coulter Elite flow cytometer using a 3-color protocol. The percentage of activated T-cell subsets, B-cells and NK-cells and the percentage increase over untreated control were calculated and plotted against compound concentrations.

Figure 2:
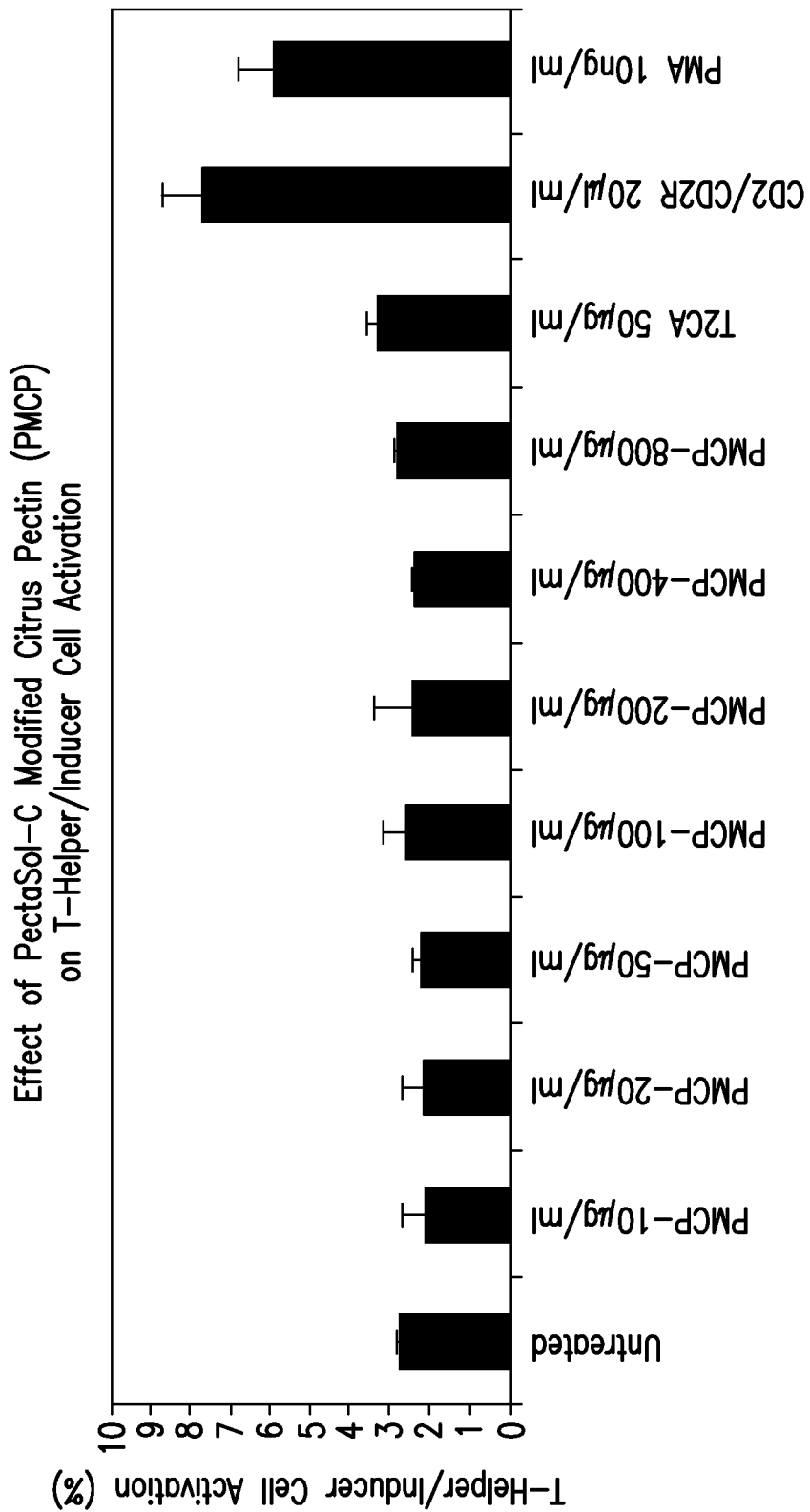
Figure 3:
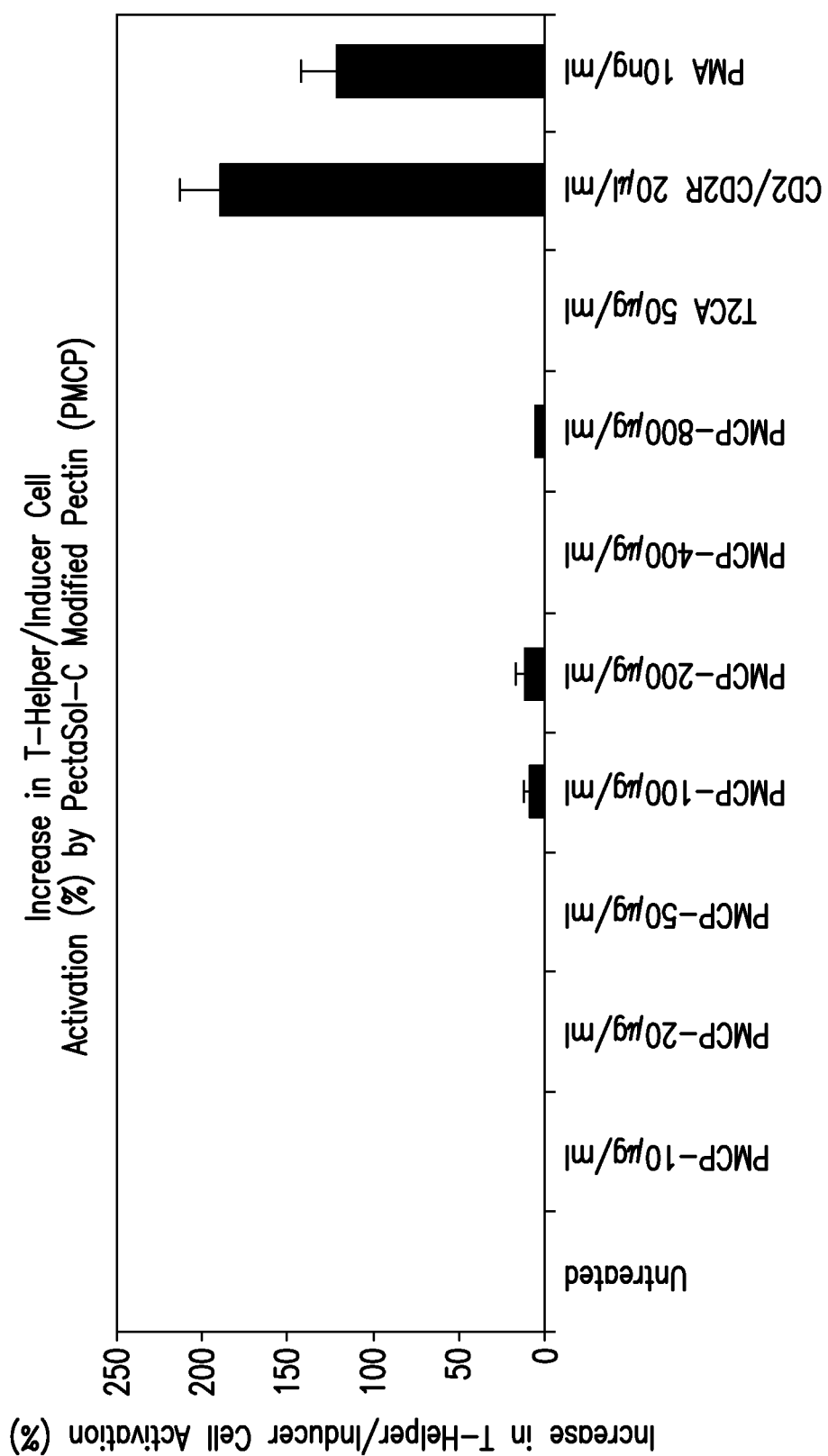
Figure 4:
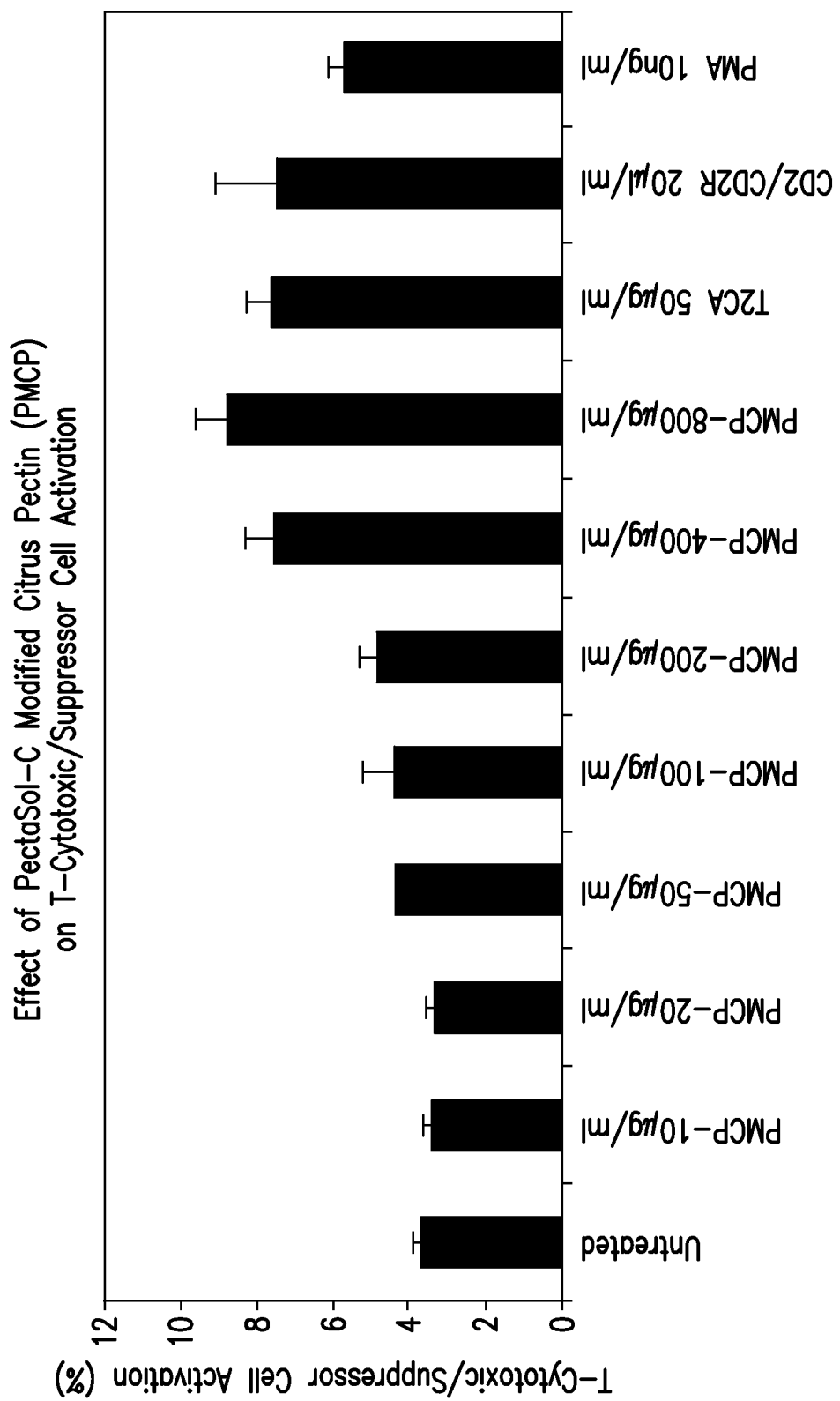
Figure 5:
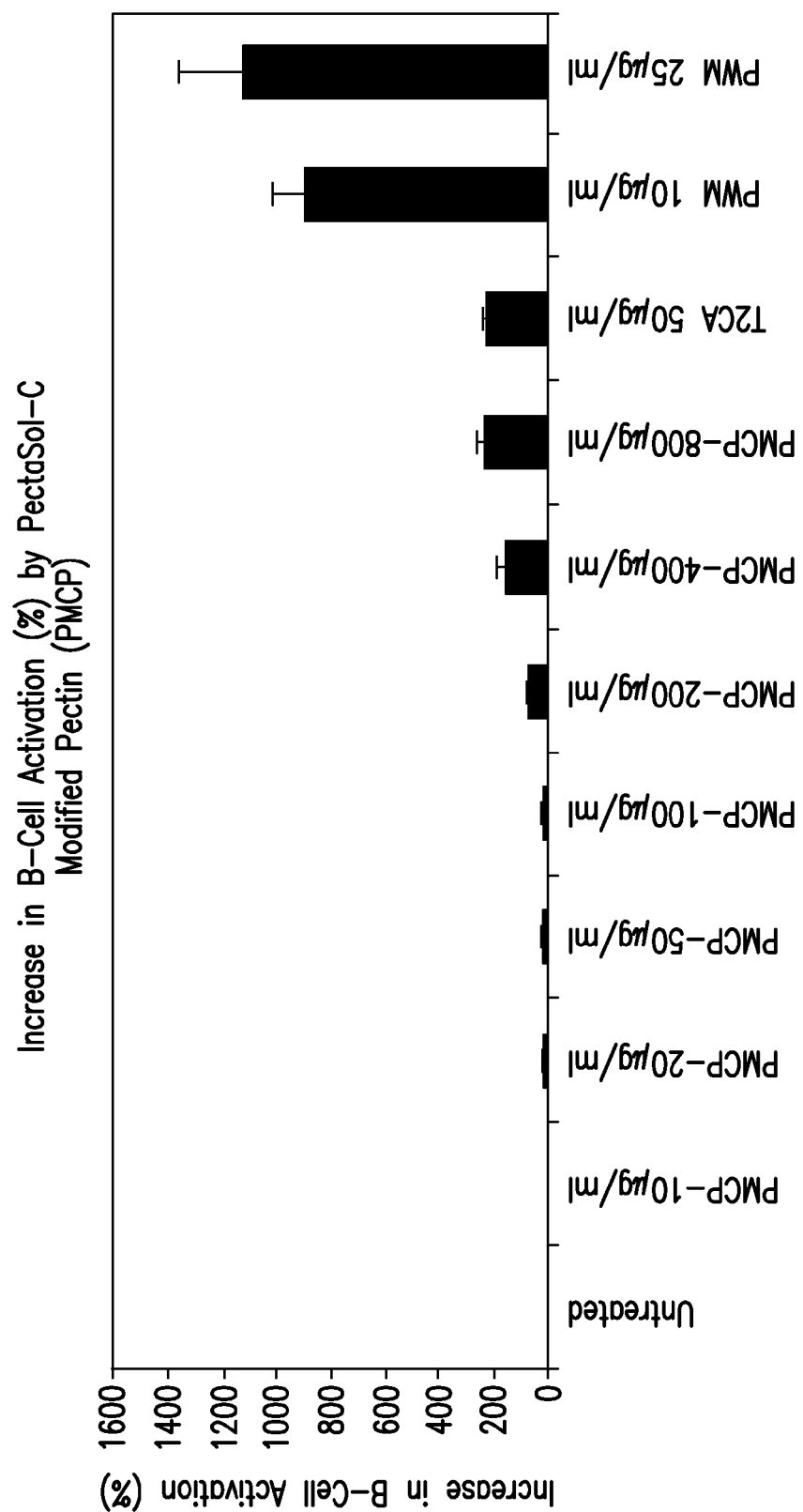

T-Lymphocyte Subset Activation:

The effects of the compound on T-helper/inducer and T-cytotoxic/suppressor cell activation are shown in Table 1 and FIGS. 2 and 3. The percent increases in T-helper/inducer lymphocyte and T-cytotoxic/suppressor cell activation are shown in Table 2 and the respective graphs in FIGS. 4 and 5. Results show that PMCP does not have a significant effect on T-helper/inducer cell activation as compared to positive controls like CD2/CD2R and PMA. However, PMCP activated T-cytotoxic/suppressor cells at lower levels and in a dose-dependent manner between 50-800 ug/ml concentrations. In this case, all three positive controls induced expected responses.

TABLE 1

Effect of PectaSol-C Modified Citrus Pectin (PMCP) on T- Helper/inducer and T- Cytotoxic/suppressor Lymphocyte Activation in Blood Cultures

| Treatment | T- helper/inducer Lymphocyte Activation | | T- cytotoxic/suppressor Lymphocyte Activation | |
|---|---|---|---|---|
| | Activation (%) | SD | Activation (%) | SD |
| Untreated | 2.70 | 0.11 | 3.68 | 0.19 |
| PMCP-10 µg/ml | 2.04 | 0.66 | 3.39 | 0.18 |
| PMCP-20 µg/ml | 2.11 | 0.56 | 3.28 | 0.24 |

TABLE 1-continued

Effect of PectaSol-C Modified Citrus Pectin (PMCP) on T- Helper/inducer and T- Cytotoxic/suppressor Lymphocyte Activation in Blood Cultures

| Treatment | T- helper/inducer Lymphocyte Activation | | T- cytotoxic/suppressor Lymphocyte Activation | |
|---|---|---|---|---|
| | Activation (%) | SD | Activation (%) | SD |
| PMCP-50 µg/ml | 2.18 | 0.25 | 4.29 | 0.02 |
| PMCP-100 µg/ml | 2.62 | 0.54 | 4.35 | 0.81 |
| PMCP-200 µg/ml | 2.43 | 0.99 | 4.75 | 0.50 |
| PMCP-400 ug/ml | 2.37 | 0.10 | 7.48 | 0.80 |
| PMCP-800 ig/ml | 2.80 | 0.13 | 8.78 | 0.81 |
| T2CA 50 µg/ml | 3.30 | 0.29 | 7.60 | 0.69 |
| CD2/CD2R 20 µl/ml | 7.72 | 1.02 | 7.42 | 1.61 |
| PMA 10 ng/ml | 5.93 | 0.89 | 5.68 | 0.45 |

TABLE 2

Increase in Percentage of T- helper/inducer and T- cytotoxic/suppressor Lymphocyte Activation by PectaSol-C Modified Citrus Pectin (PMCP)

| Treatment | T- helper/inducer Lymphocyte Activation | | T- cytotoxic/suppressor Lymphocyte Activation | |
|---|---|---|---|---|
| | % Increase | SD | % Increase | SD |
| Untreated | 0.00 | 0.00 | 0.00 | 0.00 |
| PMCP-10 µg/ml | 0.00 | 0.00 | 0.00 | 0.00 |
| PMCP-20 µg/ml | 0.00 | 0.00 | 0.00 | 0.00 |
| PMCP-50 µg/ml | 0.00 | 0.00 | 16.77 | 3.32 |
| PMCP-100 µg/ml | 7.25 | 5.13 | 19.49 | 13.78 |
| PMCP-200 µg/ml | 9.73 | 6.88 | 29.65 | 10.20 |
| PMCP-400 ug/ml | 0.00 | 0.00 | 103.11 | 5.60 |
| PMCP-800 ug/ml | 3.88 | 0.32 | 139.80 | 17.20 |
| T2CA 50 µg/ml | 22.57 | 7.79 | 107.43 | 14.72 |
| CD2/CD2R 20 µl/ml | 187.42 | 24.55 | 103.32 | 27.22 |
| PMA 10 ng/ml | 120.86 | 20.88 | 54.45 | 2.15 |

Figure 6:
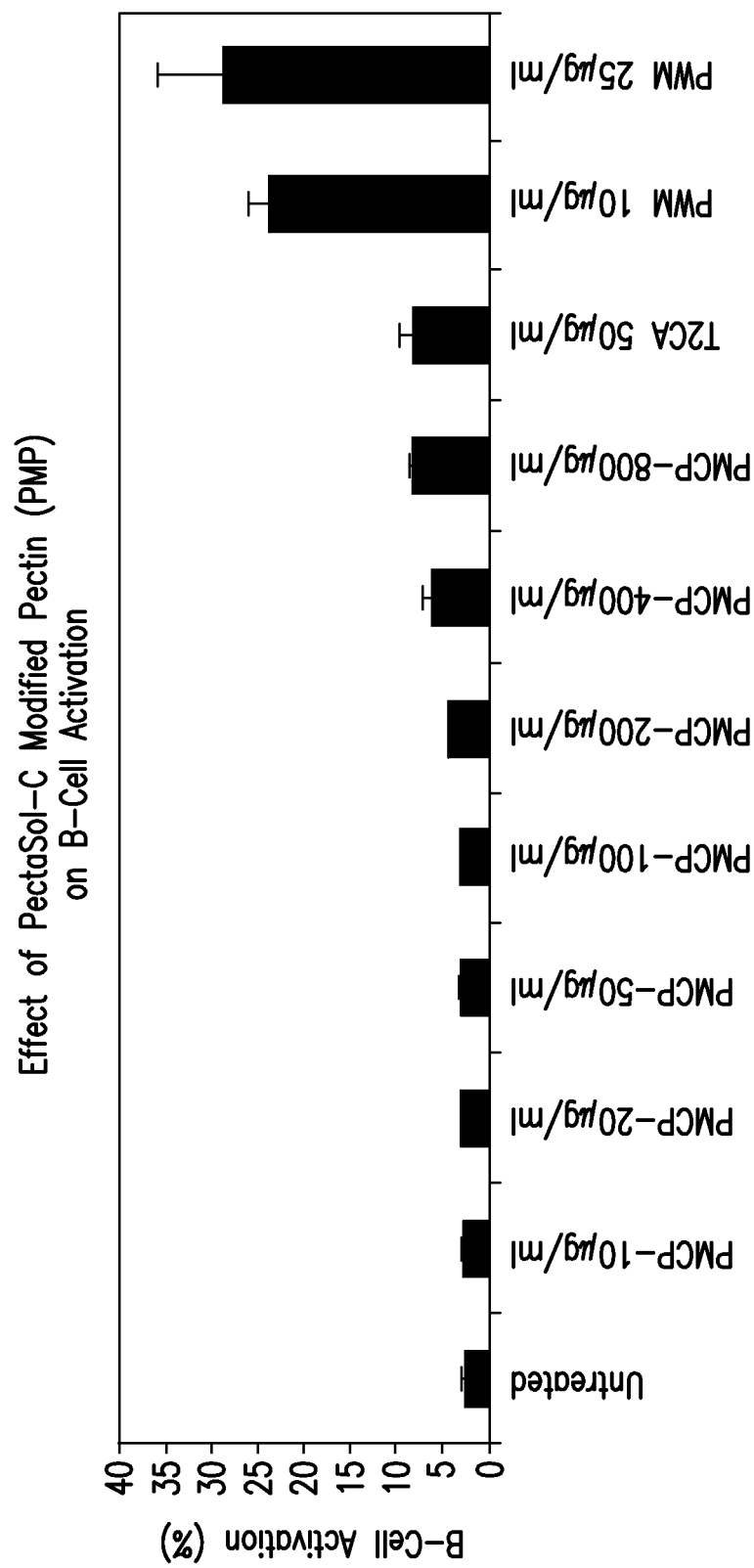
Figure 7:
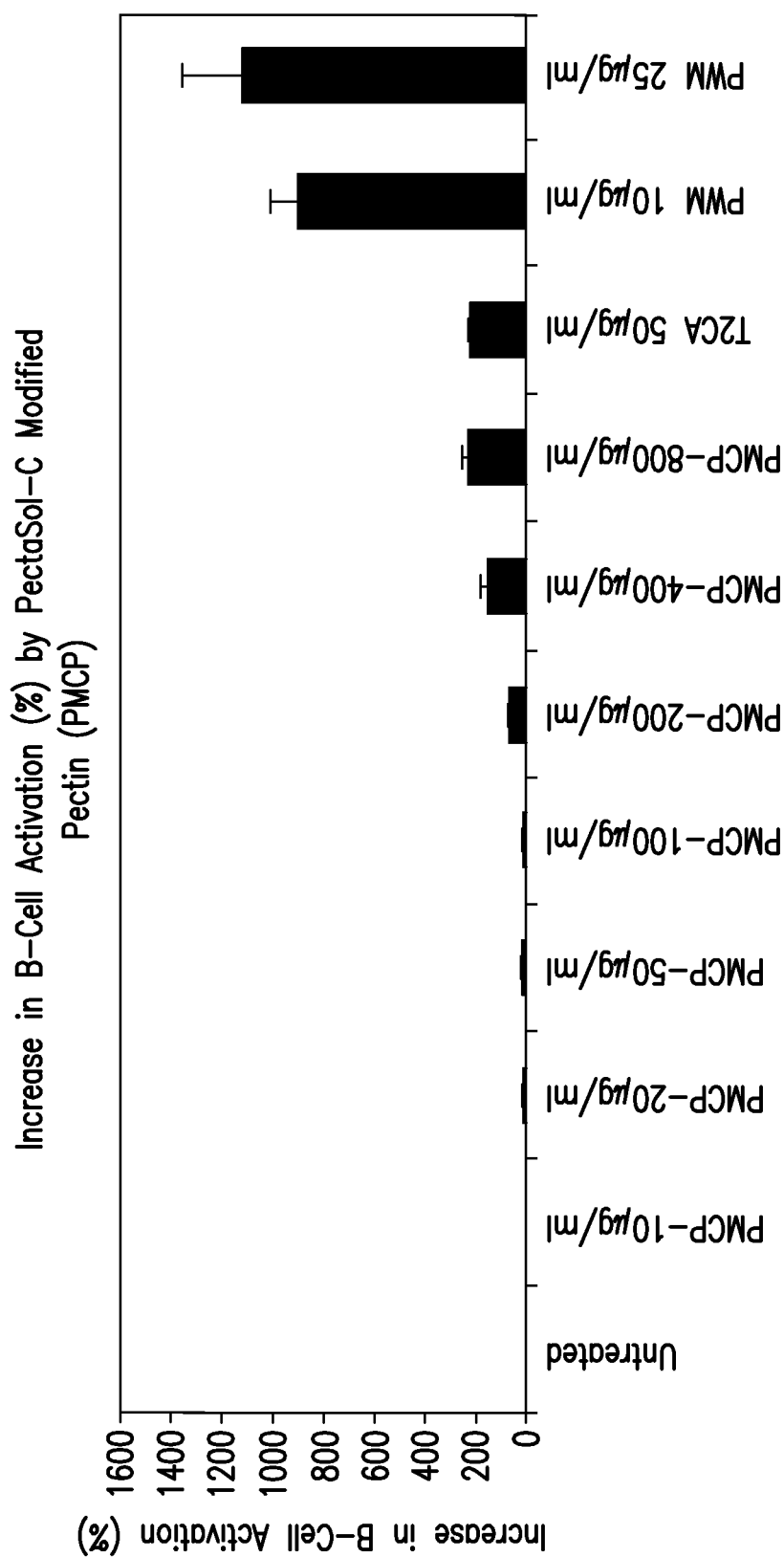

B-Cell Activation:

The B-cell activation and percentage increase over untreated control are given in Tables 3 and 4 and the respective graphs in FIGS. 6 and 7. The level of B-cell activation of by PMCP although lower than positive controls T2CA and PWM, a dose-dependent and significant increase was noticed.

TABLE 3

Effect of PectaSol-C Modified Citrus Pectin (PMCP) on B-Cell Activation

| Treatment | Activation (%) | SD |
|---|---|---|
| Untreated | 2.40 | 0.33 |
| PMCP-10 µg/ml | 2.42 | 0.26 |
| PMCP-20 µg/ml | 2.63 | 0.04 |
| PMCP-50 µg/ml | 2.75 | 0.10 |
| PMCP-100 µg/ml | 2.67 | 0.10 |
| PMCP-200 µg/ml | 3.93 | 0.04 |
| PMCP-400 ug/ml | 5.83 | 1.01 |
| PMCP-800 ug/ml | 7.73 | 0.51 |
| T2CA 50 µg/ml | 7.77 | 1.69 |
| PWM 10 µg/ml | 23.39 | 2.43 |
| PWM 25 µg/ml | 28.36 | 7.28 |

TABLE 4

Increase in Percentage of B-cell Activation by PectaSol-C Modified Pectin (PMCP)

| Treatment | % Increase | SD |
|---|---|---|
| Untreated | 0.00 | 0.00 |
| PMCP-10 µg/ml | 1.62 | 1.15 |
| PMCP-20 µg/ml | 11.57 | 8.18 |
| PMCP-50 µg/ml | 15.65 | 5.96 |
| PMCP-100 µg/ml | 12.28 | 5.72 |
| PMCP-200 µg/ml | 65.58 | 12.23 |
| PMCP-400 µg/ml | 148.54 | 38.35 |
| PMCP-800 ug/ml | 227.38 | 33.34 |
| T2CA 50 µg/ml | 222.43 | 12.91 |
| PWM 10 µg/ml | 893.23 | 119.69 |
| PWM 25 µg/ml | 1116.72 | 236.32 |

Figure 8:
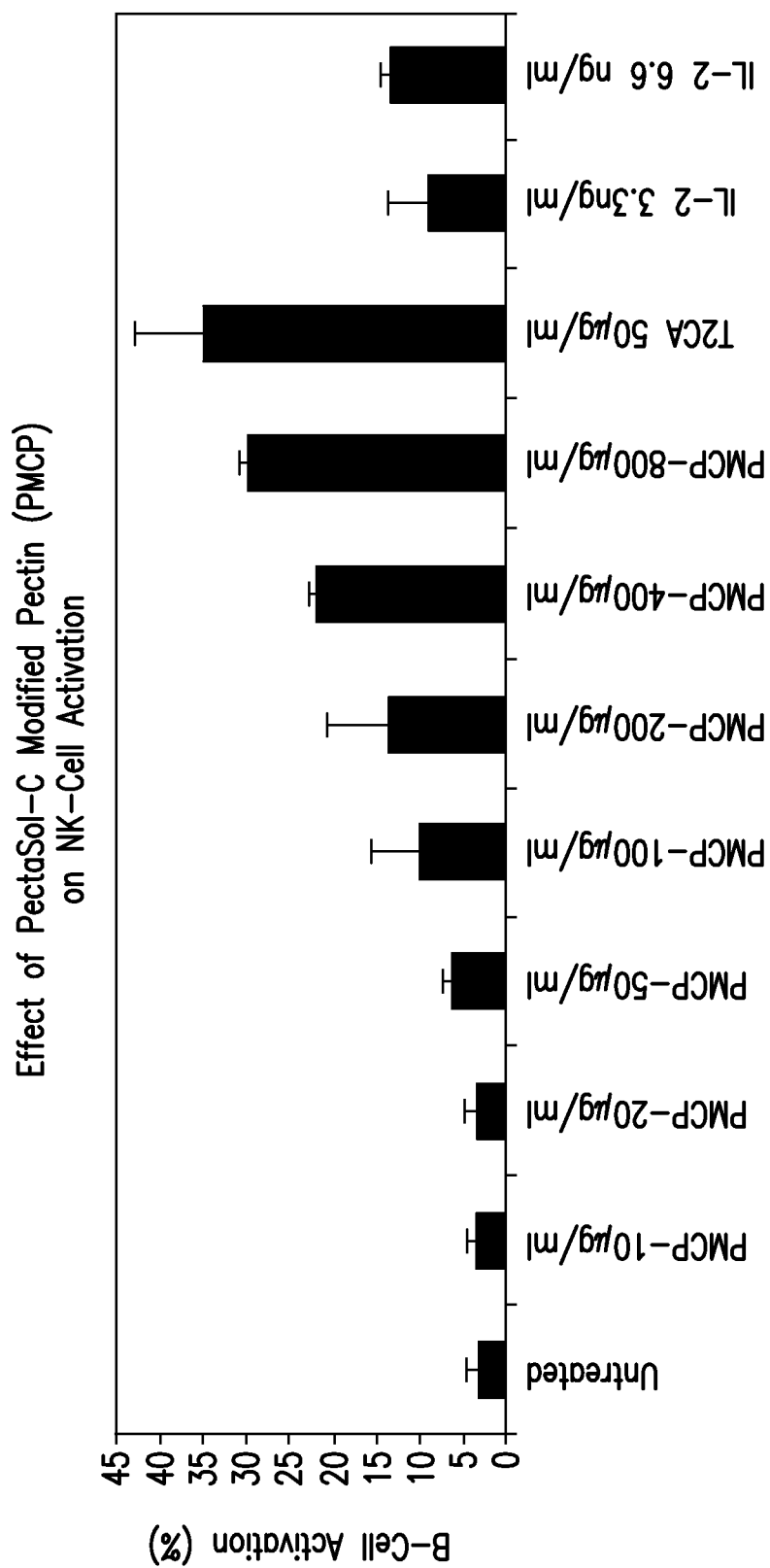
Figure 9:
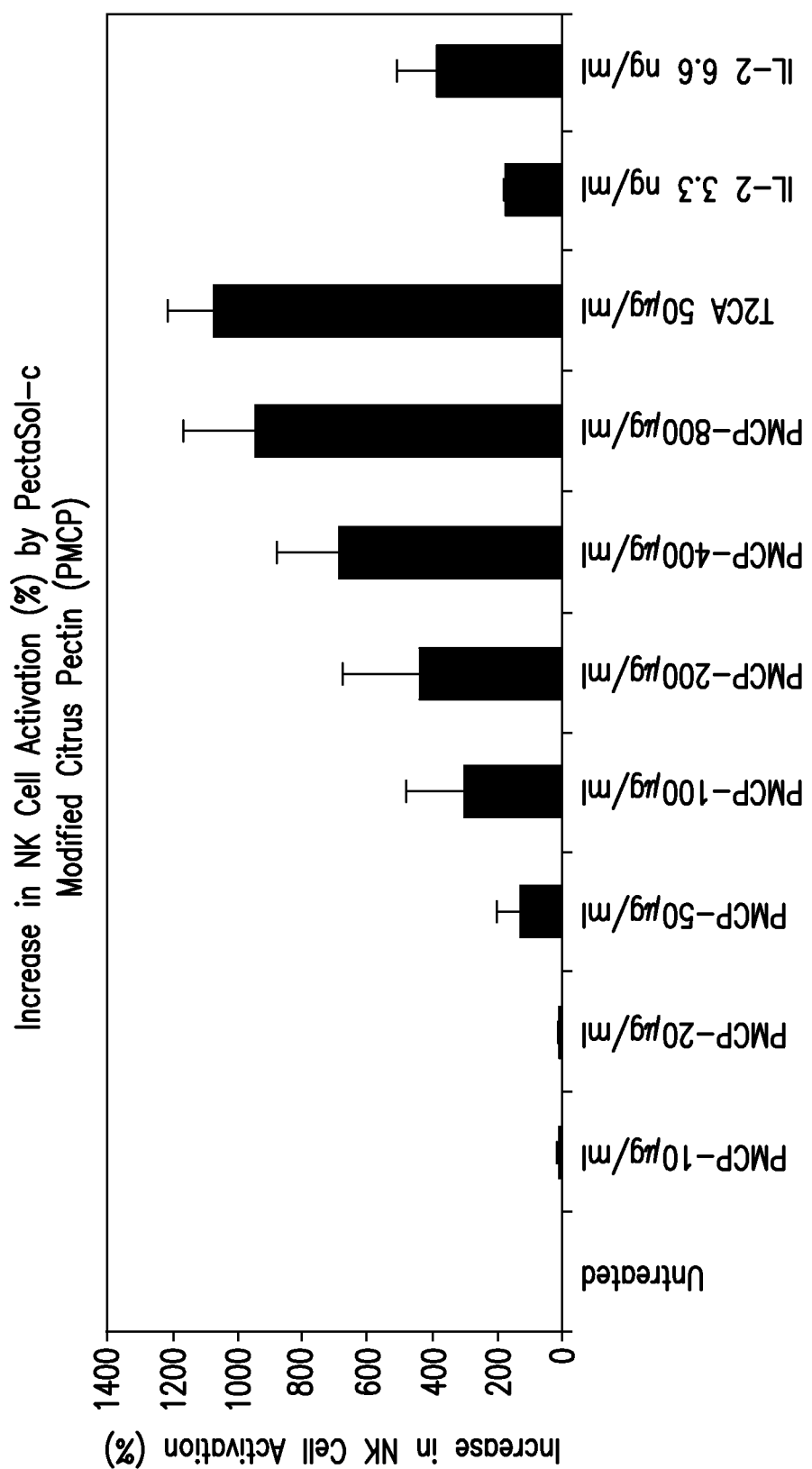

NK-Cell Activation:

The NK-cell activation data and the percentage increase over untreated control are given in Tables 5 and 6 and the respective graphs in FIGS. 8 and 9, respectively. PMCP demonstrated a good dose-dependent activation of NK-cells showing its immunostimulatory potential of the compound.

TABLE 5

Effect of PectaSol-C Modified Pectin (PMCP) on NK-cell Activation

| Treatment | Activation (%) | SD |
|---|---|---|
| Untreated | 3.14 | 1.46 |
| PMCP-10 µg/ml | 3.38 | 1.18 |
| PMCP-20 µg/ml | 3.41 | 1.34 |
| PMCP-50 µg/ml | 6.17 | 1.28 |
| PMCP-100 µg/ml | 9.85 | 5.69 |
| PMCP-200 µg/ml | 13.45 | 7.12 |
| PMCP-400 µg/ml | 21.73 | 0.89 |
| PMCP-800 ug/ml | 29.56 | 1.14 |
| T2CA 50 µg/ml | 34.67 | 7.93 |
| IL-2 3.3 ng/ml | 8.80 | 4.62 |
| IL-2 6.6 ng/ml | 13.30 | 1.12 |

TABLE 6

Increase in Percentage of NK-cell Activation by PectaSol-C Modified Pectin (PMCP)

| Treatment | % Increase | SD |
|---|---|---|
| Untreated | 0.00 | 0.00 |
| PMCP-10 µg/ml | 10.67 | 6.87 |
| PMCP-20 µg/ml | 10.45 | 4.34 |
| PMCP-50 µg/ml | 130.61 | 73.87 |
| PMCP-100 µg/ml | 298.58 | 182.98 |
| PMCP-200 µg/ml | 438.75 | 238.35 |
| PMCP-400 µg/ml | 682.86 | 195.77 |
| PMCP-800 ug/ml | 945.31 | 224.33 |
| T2CA 50 µg/ml | 1071.48 | 145.50 |
| IL-2 3.3 ng/ml | 175.65 | 9.59 |
| IL-2 6.6 ng/ml | 383.77 | 130.11 |

HNK and MCP Exhibit Synergy In the Inhibition of Cancer

To test the synergistic effects of MCP and HNK in the inhibition of cancer, liver cancer BEL-7404 cell line cells were selected for testing as a representative cancer cell line.

Experimental Procedures:

MTT assays were performed to test cell viability after treatment of MCP and HNK individually or combined.

Results

After 72 hour treatment, MCP and HNK demonstrated cytotoxicity on BEL-7404 cells in a dose dependent manner.

Figure 1B:
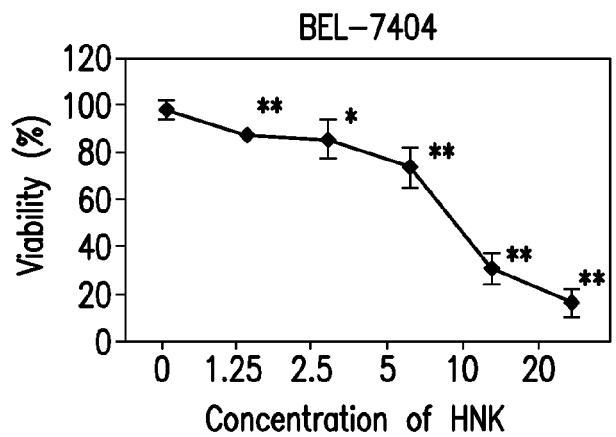
In FIGS. 1-9, the MCP administered is PectaSol-C™ modified citrus pectin or PMCP available from EcoNugenics, Inc.
Figure 1C:
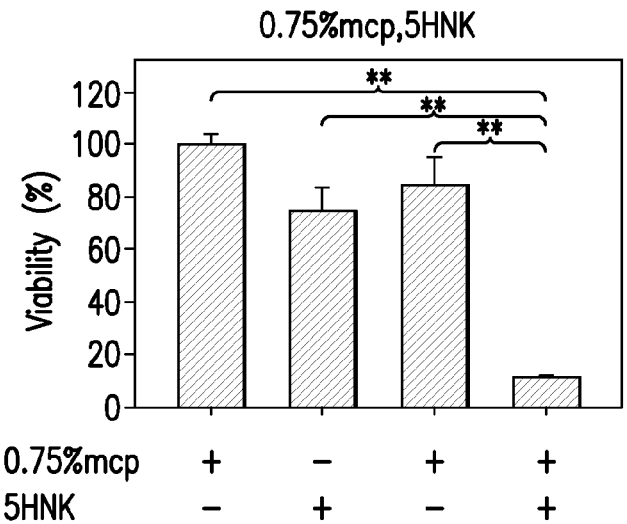

1.0% of MCP showed 51.3% of cell proliferation inhibition; while 10 µg/ml of HNK has already shown 68.7% of cell growth inhibition. When combined treatment of low doses of MCP and HNK, BEL-7404 cells showed significantly reduction of viability, compared to single treatments or vehicle treatment. The data clearly indicate that MCP and HNK have synergistic effects on BEL-7404 cells. This data is reflected in FIG. 1. As reflected in FIG. 1, in testing, 5 mcg/ml of HNK was used, and 0.75% of MCP. MCP alone had an inhibition around 20%, HNK alone around 25%, and together the inhibition increased to over 90%.

Thus, the administration of MCP improves the ability of HNK to kill cancer cells, and retard their progression. When combined in synergistic amounts, the combination of HNK and MCP or other similar pectins and alginates that are water soluble and directly metabolized and/or absorbed by mammals such as humans, commercial animals such as cows and horses and pigs, and veterinary animals like dogs and cats, inhibit the formation, progression and transformation of a wide variety of cancers. The following list is not intended to be limiting, but the combination appears effective against liver cancer, prostate cancer, breast cancer, colorectal cancer, lung cancer, melanoma, kidney cancer, etc. As the action of HNK appears directed at least in part through caspase activation, and the synergistic result of the co-administration of MCP and HNK due in part to the ability of MCP to bind Gal3 on the surface of cancers (on the surface of solid tumors where presented, and on cancer cells where the cancer is not characterized by solid tumors), and thus better present the cancer cells for HNK cytotoxicity, the synergistic combination should be generally observed against all solid tumors, as well as non-solid tumors that express Gal3 molecules on their surface, such as CLL (Chronic Lymphocytic Leukemia) and Multiple Myeloma.

MCP and HNK are both commercially available in many forms. Oral administration is preferred, but IP, IM, IV and subcutaneous administration, as well as administration across mucous membranes, for example, through rectal and vaginal suppositories, are all embraced by this invention. Superior cancer inhibition may be achieved by providing a unit dose formulation of a synergistic amount of HNK and MCP in a single tablet, capsule, powder or similar form. Thus, a capsule or tablet with a synergistic amount of HNK and MCP, either alone, or preferably in a pharmacologically acceptable carrier, is contemplated by this invention.

A daily regimen, or administration, of the synergistic combination of this invention is preferred. Larger amounts that might be used for administration on a less frequent basis may be lost through excretion, or insufficiently retained. In the alternative, more frequent administration of smaller dosages, for instance, three times daily, is clearly contemplated and envisioned, particularly for larger dosages contemplated for the embodiments of this invention where the synergistic combination is administered for the purposes of retarding or inhibiting the progress of an extant cancer, or inhibiting its transformation to a metastatic cancer.

In general, any polyuronide that is easily metabolized and water soluble, and exhibits partially esterified galacturonic acid moieties, or other moieties capable of binding Gal3 on the surface of solid tumors maybe used. A variety of pectins and alginates meeting this description are available, and discussed in the literature. While MCP is preferred as the most studied and widely available of this class of compound, others may be used in its place, or a combination of these Gal3 binding anti-cancer low molecular weight (under 40,000 daltons and preferably under 15,000 daltons) compounds may be used. Starting from the data provided in this application for patent, those of skill in the art are well enabled to calculate appropriate dosage ranges for specific types of cancers and administration protocols. Additional compounds, chemotherapeutic agents, botanicals and other agents can be added to enhance the preventative and therapeutic effects of the invention.

While the present invention has been disclosed both generically, and with reference to specific alternatives, those alternatives are not intended to be limiting unless reflected in the claims set forth below. The invention is limited only by the provisions of the claims, and their equivalents, as would be recognized by one of skill in the art to which this application is directed.

What is claimed is:

1. A method of retarding cancer progression or inhibiting transformation of a primary cancer to metastatic cancer in a mammal in need of same, comprising administering a synergistic amount of 5-500 mg/kg/day honokiol (HNK) and 15-700 mg/kg/day of modified citrus pectin (MCP), wherein the said cancer exhibits Gal3 protein on its surface and wherein the MCP exhibits the ability to bind galectin 3 (Gal3) on the surface of cancer cells for a period of time sufficient to inhibit said cancer.

2. The method of claim 1, wherein said cancer is characterized by a solid tumor.

3. The method of claim 1, wherein said cancer is a non-solid tumor cancer characterized by Gal3 protein bindable by MCP.

4. The method of claim 1, wherein said cancer is at least one of liver cancer, prostate cancer, breast cancer, colorectal cancer, stomach cancer, esophageal cancer, lung cancer, nasopharyngeal cancer, thyroid cancer, ovarian cancer, uterine cancer, multiple myeloma, leukemia, lymphoma, melanoma, sarcoma, ovarian, uterine, thyroid, brain, or kidney cancer.

5. The method of claim 1, wherein said method comprises retarding cancer progression.

6. The method of claim 1, wherein said method comprises suppressing transformation of a primary cancer to a metastatic cancer.

7. The method of claim 1, wherein said method comprises inhibiting the spread of metastatic cancer.

8. A composition of matter comprising an amount of 5-500 mg/kg/day honokiol (HNK) and 15-700 mg/kg/day of modified citrus pectin (MCP), which, when administered to a mammal with cancer, provides a synergistic degree of cancer inhibition in excess of the inhibitory effects achieved by the administration of HNK or MCP alone, wherein the mammal in need of same, wherein the said cancer exhibits Gal3 protein on its surface and wherein the MCP exhibits the ability to bind galectin 3 (Gal3) on the surface of cancer cells for a period of time sufficient to inhibit said cancer.

9. The composition of claim 8, wherein said composition is in the form of a tablet, capsule, suppository or powder.

10. The composition of claim 8, wherein said tablet, capsule, suppository or power for daily consumption by a mammal in need of cancer inhibition.

11. The composition of claim 10, wherein said tablet, capsule, suppository or powder is provided with HNK and MCP in an amount such that 2-5 doses consumed daily provide 10-500 mg/kg/day HNK and 15-700 mg/kg/day MCP.

12. The method of claim 1, wherein said administration is accompanied by administration of an agent established to have anti-cancer effectiveness at a given level.

13. The method of claim 12, wherein said agent is administered at a level that is below a level where said agent may be toxic to said mammal, but is effective in further inhibiting cancer when administered with a synergistic combination of HNK and MCP.

14. The method of claim 12, wherein said agent is a chemotherapeutic agent.

15. The method of claim 12, wherein said agent comprises anti-cancer radiation therapy.

16. The method of claim 12, wherein said agent comprises an immunotherapy or biologic anti-cancer therapy.

\* \* \* \* \*